United States Patent [19]
Vancaillie et al.

[11] Patent Number: 5,620,010
[45] Date of Patent: Apr. 15, 1997

[54] DISPOSABLE SURGICAL DRAPE

[75] Inventors: Thierry G. Vancaillie, San Antonio, Tex.; Robert K. Mitchiner, Longmont, Colo.

[73] Assignee: Aquintel, Inc., Mountain View, Calif.

[21] Appl. No.: 617,352

[22] Filed: Mar. 18, 1996

Related U.S. Application Data

[63] Continuation-in-part of Ser. No. 109,121, Aug. 19, 1993, Pat. No. 5,395,354.
[51] Int. Cl.⁶ ........................................ A61G 15/00
[52] U.S. Cl. ............................... 128/845; 128/849
[58] Field of Search .......................... 128/849–856, 128/845, 846

[56] References Cited

U.S. PATENT DOCUMENTS

| 4,414,968 | 11/1983 | Amin | 128/853 |
|---|---|---|---|
| 4,598,458 | 7/1986 | McAllester | 128/853 |
| 5,445,165 | 8/1995 | Fenwick | 128/853 |
| 5,522,403 | 6/1996 | Bark | 128/853 |

*Primary Examiner*—Michael A. Brown
*Attorney, Agent, or Firm*—Akin, Gump, Strauss, Hauer & Feld, L.L.P.

[57] ABSTRACT

A disposable surgical drape having a folding funnel, folding frame means, and splash shield functions as a fluid collector for use during surgery. A portion of the splash shield is placed under the patient while the remainder extends over the operating table end to direct fluid flow to a folding funnel which is shaped and positioned as desired with folding frame means. Fluid draining into the funnel is collected for measurement. Folding frame means impart a substantially frusto-conical or frusto-pyramidal shape to the funnel in use and employ one or more hinged struts to help maintain the funnel mouth substantially open and horizontal.

6 Claims, 2 Drawing Sheets

DISPOSABLE SURGICAL DRAPE

This application is a continuation-in-part of application Ser. No. 08/109,121, filed 19 Aug. 1993, now U.S. Pat. No. 5,395,354.

BACKGROUND

FIELD OF THE INVENTION

The invention relates to surgical drapes for maintenance of a surgical field and for collection of waste fluid.

Waste Fluid in Surgery

Irrigation fluid is commonly used in open surgery as well as in endoscopic examination and surgery performed on the vagina and uterus (transvaginally) and on the urethra and bladder (transurethrally). Any such anatomic approach requires sufficient dilation or spreading of the tissues to allow manipulation of the surgical instruments and to give the surgeon visibility to properly perform the surgery. In an anesthetized patient, clamps and/or retractors are used to maintain open surgical access and a weighted speculum is commonly employed to maintain the desired degree of vaginal dilation. A urethra is typically progressively dilated just prior to insertion of an endoscope guide tube.

Waste irrigation fluid drains at least intermittently from open surgical sites, as well as through and around the endoscope during transvaginal and transurethral endoscopic surgery. An intermittent or continuous flow of water-based (generally nonconducting) irrigation fluid from an external reservoir is directed to the surgical site by tubing, syringes, small containers or through the endoscope. Waste irrigation fluid drains, in turn, from the open surgical access, the vagina or the urethra.

Irrigation fluid flow in the area of surgery removes small pieces of excised tissue and blood, continually clearing the surgeon's view of the operative site(s). Most of the irrigation fluid which flows to the operative site is subsequently flushed out by additional irrigation fluid, but a portion of the entering fluid may be absorbed through the tissue surfaces of the operative site and through parts of the patient's vascular system exposed by the surgery.

During relatively prolonged and/or invasive surgery, sufficient fluid may be absorbed to substantially adversely alter the patient's serum electrolyte balance. Because serious electrolyte imbalances may result in seizures, coma or death of the patient, the surgeon must have sufficient warning of impending fluid overload to take corrective action. While this can be accomplished through frequent estimates of serum electrolyte levels during the surgical procedures, an easier and less expensive method involves estimation of the amount of fluid absorbed. In turn, this requires accurate estimates of the difference in the amounts of irrigation fluid administered and waste irrigation fluid lost. If blood loss can be accurately estimated or is clinically insignificant, the irrigation fluid difference can serve as an estimate of absorbed irrigation fluid. Errors in estimating the difference most often arise in estimating the amount of irrigation fluid lost because such fluid is typically hard to recover completely.

A fraction of the drained waste irrigation fluid typically falls on surgical drapes and thence to the operating table or floor, where it is commonly lost without being measured. Because the volume of this lost fraction of waste fluid is generally unknown, the amount of irrigation fluid absorbed by the patient is difficult to estimate accurately during the course of an operation.

SUMMARY OF THE INVENTION

The present invention relates to apparatus for collecting and measuring waste irrigation fluid drained from a surgical site, including that draining from an endoscope, urethra or vagina and otherwise released in connection with the use of endoscopic instruments for surgery. Accurate measurement of waste irrigation fluid volume facilitates estimation of the amount of irrigation fluid absorbed by a patient, and the present invention comprises surgical drapes and related apparatus to facilitate collection and measurement of waste irrigation fluid.

A preferred embodiment of a disposable surgical drape of the present invention comprises a splash shield, folding funnel and folding frame means. These components are made to be coupled adhesively in certain preferred embodiments so that the pieces may be interchanged and/or purchased separately. The splash shield and folding funnel are preferably fabricated substantially of sheet plastic and/or non-woven sheet material which has been treated for water resistance.

The splash shield may be substantially flat or it may have edges gathered substantially in the manner of a fitted sheet. It is intended for substantially horizontal placement under a patient to direct waste irrigation fluid flow to the folding funnel. Typically, the splash shield will be placed under a patient in the lithotomy position and extend substantially to or over the end of the operating table facing the surgeon. The splash shield is preferably wide enough to catch substantially all waste irrigation fluid draining from the patient which does not fall directly into the funnel portion.

Waste fluid falling on the splash shield when it is substantially horizontal will tend to flow toward the center line of the operating table due to the weight of the patient which compresses the table pads together with the splash shield portion which lies between the patient and the table pads. Waste fluid on the splash shield will further tend to flow toward the end of the operating table facing the surgeon or toward the other end of the table, depending on how the table is tilted. That which flows toward the surgeon tends to flow over at least a portion of the folding frame means and into the funnel. For this reason, a drip shield which loosely falls over the upper portion of the folding frame base may optionally be sealingly coupled to the splash shield to facilitate fluid flow over the folding frame means. The drip shield is preferably coupled to the splash shield by heat sealing or an analogous process which produces a highly water-resistant bond. When so used, the drip shield will tend to shield from water damage or leakage the (preferably adhesive) coupling of the folding frame means to the folding funnel, as well as the (preferably adhesive) coupling of the folding funnel mouth to the splash shield.

A folding funnel receives fluid flow from the splash shield, the folding funnel comprising a funnel body having a funnel mouth and a funnel mouth edge. At least a portion of the funnel mouth edge is sealingly coupled to the splash shield (as, for example, by heat sealing of sheet plastic or, preferably, by use of water-resistant adhesives). The folding funnel is so constructed as to have a substantially frusto-conical or frusto-pyramidal shape when suspended freely under the influence of gravity with the plane of the funnel mouth uppermost and substantially horizontal. A sufficient length of funnel mouth edge is sealingly coupled to the splash shield to ensure that substantially all fluid flow over the end of the operating table facing the surgeon will enter the folding funnel, assuming the funnel mouth is being held substantially open by the folding frame means.

Folding frame means are coupled to the folding funnel for the purpose of holding open the funnel mouth. Folding frame means comprise a substantially planar (preferably plastic) base which is relatively rigid compared to the sheet material of the splash shield and folding funnel. The base has a first end, a second end, a substantially centered longitudinal axis extending between the first and second ends, and a longitudinal bending compliance along the longitudinal axis. Additionally, folding frame means comprise at least one resilient elongated strut, each strut having a proximal end and a distal end and a longitudinal bending compliance greater than the base longitudinal bending compliance, each strut proximal end being coupled to the base. Each strut distal end comprises edge coupling means for coupling the strut to a funnel mouth edge, and hinge means are used for coupling each strut to the base. Hinge means may include, for example, a thinned section of relatively thicker plastic material (a living hinge) or a hinge of conventional design (analogous to a piano hinge). To maintain the folding funnel in a preferred orientation during use, strut hinge means may preferably be designed to transmit torque in a substantially vertical plane.

Edge coupling means may comprise, for example, a protrusion of reduced cross-sectional area (relative to the strut) which projects from the distal end of the strut to engage a hole in the funnel mouth edge. Alternatively, edge coupling means may comprise an adhesive area on the distal strut end to bond with a portion of the funnel mouth edge. Still another alternative edge coupling means may comprise a hook-and-loop area on the distal strut end (covered, for example, with Velcro) to adjustably attach to a corresponding portion of the funnel mouth edge having a mating hook-and-loop area.

Struts are intended to fold compactly against the base for shipment and storage and to hold the funnel mouth open during use of the disposable surgical drape, preferably so that the funnel mouth edge is in tension sufficient to keep it from sagging noticeably. Ideally, struts would be substantially straight while maintaining the desired edge tension, but to allow for manufacturing tolerances in the funnel edge length, struts will preferably experience more or less longitudinal bending under a compressive load caused by the edge tension. Such longitudinal bending will result in a shortened straight-line distance between proximal and distal ends of a strut (effectively, "strut shortening") relative to the strut length when straight. The degree of bending compliance is then conveniently measured in units of strut shortening per unit of compressive load. Slightly undersized funnel mouths will resulting in relatively greater compressive loads and thus more strut shortening, while slightly oversized mouths will result in relatively smaller compressive loads and thus less strut shortening.

Preferred embodiments of the folding frame means comprise from one to three struts including, for example, first and second resilient elongated struts having lengths and longitudinal bending compliances that are substantially equal. A third resilient elongated strut may be added having a longitudinal bending compliance greater than the first strut longitudinal bending compliance and length greater than the first strut length to attain certain desired funnel mouth shapes.

Note that certain preferred embodiments of the invention may also (or alternatively) incorporate a predetermined compliance in tension (units of elongation per unit of tension load) in the funnel mouth edge. Further, the funnel mouth edge may be designed to have a non-uniform compliance in tension when it is desirable to maintain certain portions of the funnel mouth opening as having a highly repeatable appearance, notwithstanding the effects manufacturing tolerances on strut length and funnel mouth edge length. Non-uniform compliance in tension is preferably achieved, for example, by coupling (as by heat sealing) elongated resilient tension members such as plastic or rubber strips to one or more predetermined portions of the funnel mouth edge.

Folding frame means may optionally additionally comprise a longitudinally hinged portion of the base to which all elongated struts are coupled for adjusting elevation of each strut. The (preferably living) hinge is preferably located along at least a portion of the superior edge of the hinged portion. When, for example, struts extend substantially perpendicularly from a longitudinally hinged portion of a base, adjustment of strut elevation can bring each strut into a substantially horizontal position. Since in use, struts will normally lie substantially in the plane of the funnel mouth, the funnel mouth can be made substantially horizontal (its preferred orientation in use). To keep the funnel mouth substantially horizontal, an elongated hinge lock (preferably in the form of a rod or bar) maintains the adjustment of the longitudinally hinged portion when it is present by either preventing it from closing (that is, moving toward a substantially coplanar position with the remainder of the base), or preventing it from opening. In the former case, the elongated hinge lock is adjustably coupled to the base in such a position as to keep the hinged portion of the base from being completely closed. Such hinge lock coupling to the base can conveniently be achieved through hook-and-loop areas of the hinge lock ends and corresponding portions of the base in contact with the hinge lock ends.

In use with the funnel mouth substantially horizontal as described above, the funnel weight acts through the strut(s) to create a bending moment tending to rotate the base around an axis substantially parallel to its longitudinal axis (thus distorting the splash shield to which the base is coupled). To resist such a bending moment, the folding frame means base may comprise at least one stiffener to aid in maintaining a desired elevation of each resilient strut. Stiffeners are (preferably substantially coplanar) projections from the base that may be coupled to the splash shield in the same manner as the base or may simply rest against it if the applied bending moment will tend to move the stiffener toward the splash shield. By increasing the degree of rotational coupling of the base to the splash shield, the latter structure may exert greater compensating torque on the base which will tend to hold the funnel mouth substantially horizontal.

Another structure which may be used (alone or in conjunction with the above stiffeners) to counteract the above base bending moment in surgical drapes of the present invention comprises at least one elongated suspension strap adjustably coupling the splash shield and the folding frame means for holding the open funnel mouth substantially horizontal. Adjustability of the coupling may be attained through use of, for example, hook-and-loop fasteners (such as Velcro) or adhesive pads on one or both suspension strap ends and/or the splash shield. Suspension straps, of course, are preferably adjustably coupled to struts and may conveniently be adhered to or looped around them, the latter providing a sliding adjustment. When this loop-adjustment embodiment is preferred, struts and/or the suspension straps, which adjustably slide over and support them may incorporate relatively high-friction surfaces to provide a relatively stable (but easily changed) adjustment after the strap is placed in tension due to the load imposed by holding the funnel mouth substantially horizontal.

DETAILED DESCRIPTION

Figure 3:
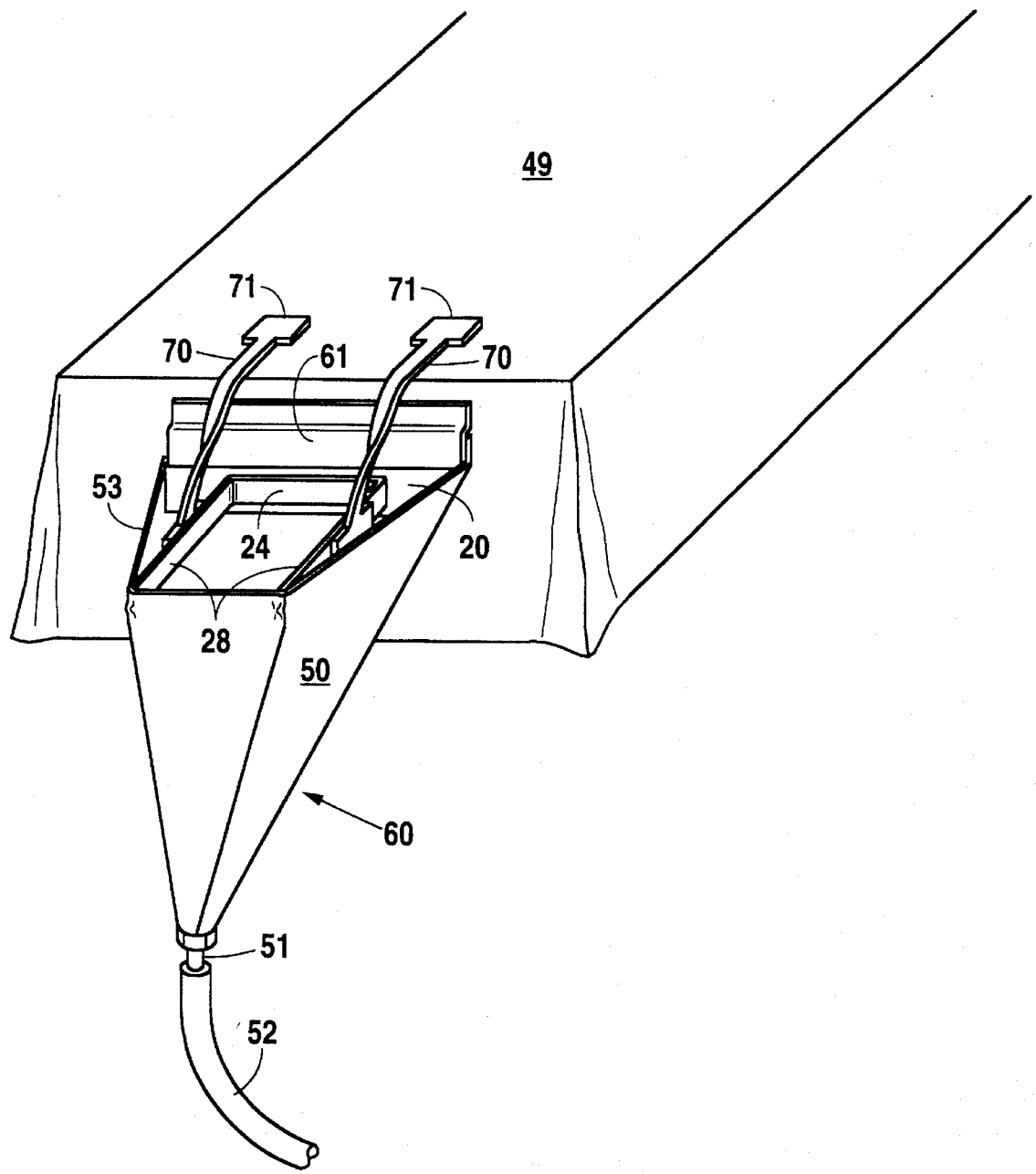
FIG. 3 schematically illustrates a disposable surgical drape prepared for use and incorporating optional suspension straps.

Disposable surgical drapes of the present invention comprise a splash shield 49, folding funnel 60 and folding frame means 10. The splash shield 49 is for substantially horizontal placement in use as shown in FIG. 3, and the folding funnel 60 is for substantially vertical placement in use (also shown in FIG. 3). While optionally being sold and/or shipped separately, the folding funnel 60 in use is sealingly (preferably adhesively) coupled to the splash shield 49, with the folding frame means 10 sealingly (preferably adhesively) coupled to the folding funnel 60. Note that the folding frame means may optionally be placed so as to be directly in contact with (and coupled to) the folding funnel 60 only or both the folding funnel 60 and the splash shield 49.

Figure 2A:
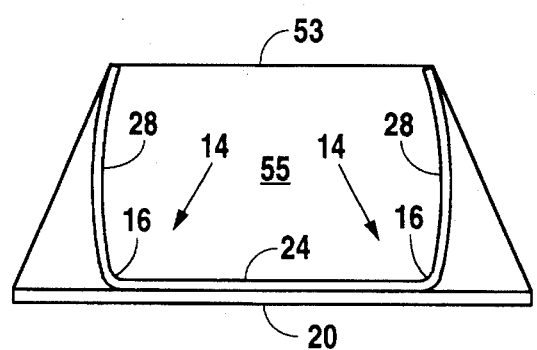
FIGS. 2A–C schematically illustrate plan views of various representative funnel mouth configurations achievable in disposable surgical drapes of the present invention.
Figure 2B:
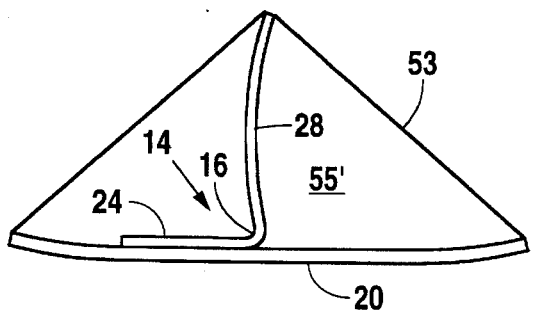

The folding funnel 60 comprises a funnel body 50 having a funnel mouth 55,55',55" which is a substantially planar area enclosed by a funnel mouth edge 53. Note that through various arrangements of struts 28,28' in relation to the base 20 of folding frame means 10, funnel mouth 55,55',55" can be given various shapes (three examples of such shapes being schematically illustrated in FIGS. 2A–C). The above surgical drape may optionally additionally comprise a drip shield 61 sealingly coupled to splash shield 49 to facilitate fluid flow over the base 20 of folding frame means 10. Other optional components of the above surgical drape are funnel drain connector 51 (which couples funnel body 50 with funnel drain hose 52) and elongated suspension straps 70 (FIG. 3) for adjustably coupling splash shield 49 and folding frame means 10 for holding funnel mouth 55,55'55" substantially horizontal in use. Note that suspension straps 70 are preferably coupled to splash shield 49 through coupling areas 71 (which may comprise, for example, adhesive portions or hook-and-eye portions for coupling with corresponding portions on splash shield 49). At the ends of suspension straps 70 opposite coupling areas 71, the straps will preferably be coupled to struts 28,28' as desired in an analogous manner or by looping straps 70 around struts 28,28' and coupling the strap ends to the straps 70 themselves in the manner described above.

Figure 1:
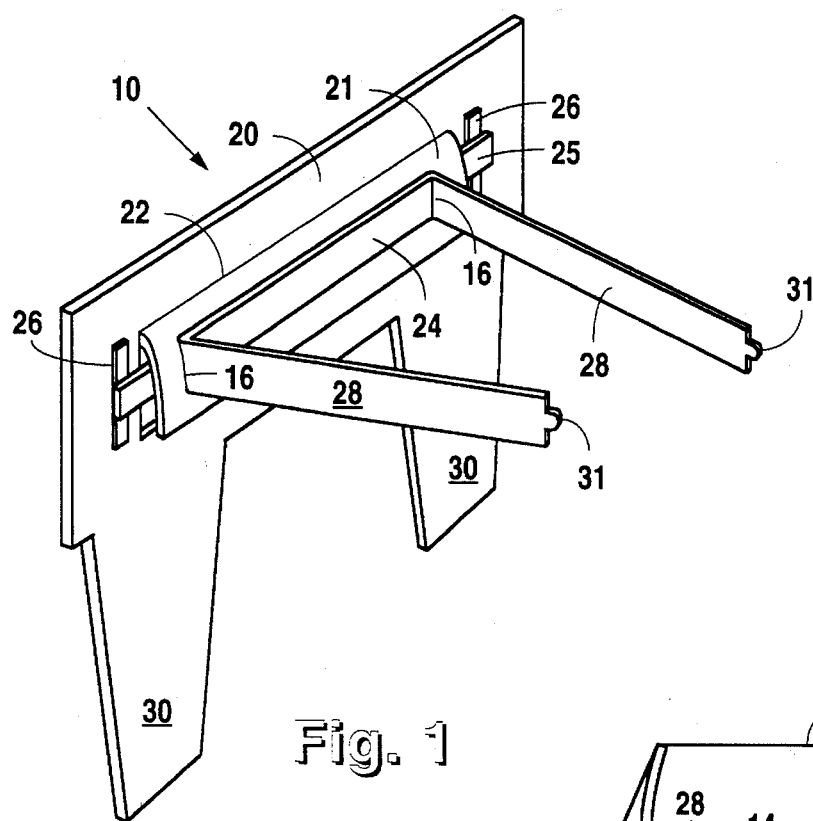
FIG. 1 schematically illustrates a preferred embodiment of the folding frame means comprising optional stiffeners.

Folding frame means 10 as schematically illustrated in FIG. 1 comprises a base 20 and two resilient elongated struts 28. Each strut 28 distal end comprises edge coupling means 31 for coupling the strut 28 to a funnel mouth edge 53. Hinge means 14,14' comprise a proximal portion 24,24' which is coupled (as by plastic welding or gluing) to base 20 and includes joint 16,16'. Joint 16,16' may comprise, for example, a thinned section of relatively thicker plastic material (a living hinge joint) or a hinge joint of conventional design (analogous to a piano hinge joint). Note that the living hinge joints 16 schematically illustrated in FIG. 1 are designed to transmit torque in a substantially vertical plane (that is, in use they resist the tendency of any weight applied to struts 28 (such as a folding funnel 60) to pull the struts 28 below a horizontal plane.

Figure 2C:
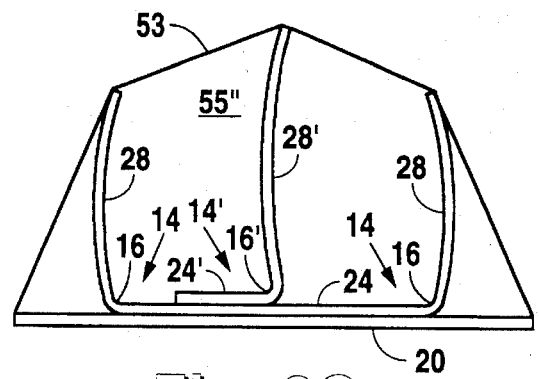

Another feature of the present invention which can be used to keep struts 28,28' in a substantially horizontal plane is the longitudinally hinged portion 21 of base 20. FIG. 1 schematically illustrates the superiorly located hinge 22 as well as elongated hinge lock 25 for maintaining adjustment of longitudinally hinged portion 21. Elongated hinge lock 25 is shown as being adjustably coupled (through areas adjacent its ends) to corresponding coupling areas 26 of base 20. Other features of the present invention which can be used to keep struts 28,28' in a substantially horizontal plane are the stiffeners 30 (also shown in FIG. 1). Note that when a third resilient elongated strut 28' is placed between two relatively shorter struts 28 as schematically illustrated in FIG. 2C, the funnel mouth 55" which is created is relatively deeper than the corresponding funnel mouth 55 which is created by two struts 28 (schematically illustrated in FIG. 2A). The deeper funnel mouth 55" will tend to exert a greater bending moment on base 20 than funnel mouth 55. To resist a greater bending moment, each strut may preferably have an "I" beam or "H" beam cross-section to resist bending along its longitudinal axis in a substantially vertical plane under the weight of the funnel (i.e., relatively low vertical bending compliance), while at the same time having a substantially greater longitudinal bending compliance in a substantially horizontal plane (i.e., relatively high horizontal bending compliance).

Edge coupling means 31 (shown in FIG. 1) are intended to reversibly prevent lateral movement of the distal end of a strut 28,28' with respect to a portion of the funnel mouth edge 53. Edge coupling means 31 may comprise a small protrusion at the distal end of a strut 28 (as schematically illustrated), the protrusion being sized to allow its insertion into a properly located and closely fitting hole in the funnel mouth edge 53. Edge coupling means may also comprise a socket portion molded into or otherwise coupled to the funnel mouth edge, the socket portion reversibly coupling (preferably with a snap or friction fit) a ball portion located at a strut 28,28' distal end. Still another embodiment of edge coupling means 31 may comprise a separate socket portion which can be reversibly applied to a ball portion on a strut 28 distal end with a portion of the funnel mouth edge 53 reversibly trapped between the ball portion and the socket portion. The latter edge coupling means 31 embodiment is intended to be adjustably applicable to any of a plurality of locations on the funnel mouth edge 53. Note that the ball and socket need not be spherical or smooth, but may be substantially ellipsoidal or substantially cylindrical or may comprise one or more solid angles to enhance its anchoring function and/or its reversible coupling function.

In general, a strut 28,28' substantially crosses from one portion of the funnel mouth 55,55',55" to another portion. The funnel mouth 55,55',55" is preferably maintained open in some desired shape and in tension by the combined resilience of the base 20 and one or more struts 28,28'. While longitudinal (that is, bending) compliance of both the base 20 and struts 28,28' contributes to shaping of the funnel mouth, strut longitudinal compliance exceeds base longitudinal compliance in preferred embodiments. Note also that certain portions of the funnel mouth edge 53 may preferably have greater compliance in tension than adjacent portions, the non-uniform compliance in tension being useful in compensating for manufacturing tolerances in various portions of the disposable surgical drape while assuring a substantially repeatable and predetermined funnel mouth shape.

The present invention is particularly adapted for use with a malleable speculum during transvaginal endoscopic surgery. A malleable speculum may be used independently or may be sealingly coupled either reversibly or substantially irreversibly to an apron-funnel-splash shield assembly to facilitate collection of waste fluid drainage (see U.S. Pat. No. 5,395,354, Mar. 7, 1995, Vancaillie, a divisional of application Ser. No. 08/109,121, filed 19 Aug. 1993, incorporated herein by reference). The malleable speculum may be used without the apron-funnel-splash shield assembly for operations wherein accurate estimation of the amounts of drained and absorbed irrigation fluid is regarded as unnecessary because the absorption of clinically significant amounts is unlikely. However, because the duration and/or invasive character of a surgical procedure may be difficult to precisely predict, a requirement for collection and accurate measurement of drainage fluid is often presumed. Thus, the malleable speculum may be present in a preferred embodiment of the present invention as part of a drape assembly comprising a speculum, an apron, a folding funnel, a splash shield, and folding frame means. This assembly acts to provide the desired degree of vaginal dilation and to improve the accuracy of fluid absorption estimates during endoscopic surgery. The latter function includes collecting and measuring both the irrigation fluid which falls directly on components of the drape assembly and that which reaches the drape assembly after flowing over the patient or portions of the surgical and operating room support apparatus associated with the operation.

What is claimed is:

1. Folding frame means, comprising
    a base having a first end, a second end, a substantially centered longitudinal axis extending between said first and second ends, and a longitudinal bending compliance along said longitudinal axis;
    at least one resilient elongated strut, each strut having a proximal end and a distal end and a longitudinal bending compliance greater than said base longitudinal bending compliance, each said strut proximal end being coupled to said base, wherein each said strut distal end comprises edge coupling means for coupling said strut to a funnel mouth edge; and
    hinge means for coupling each said strut to said base.

2. The folding frame means of claim 1, additionally comprising
    a longitudinally hinged portion of said base to which all elongated struts are coupled for adjusting elevation of said at least one resilient strut; and
    an elongated hinge lock for maintaining adjustment of hinge portion, said elongated hinge lock being adjustably coupled to said base.

3. The folding frame means of claim 1 wherein said base comprises at least one stiffener to aid in maintaining elevation of said at least one resilient strut.

4. The folding frame means of claim 1 comprising first and second resilient elongated struts, wherein said first and second strut longitudinal bending compliances are substantially equal.

5. The folding frame means of claim 4, wherein said first and second strut lengths are substantially equal.

6. The folding frame means of claim 5 further comprising a third resilient elongated strut having a longitudinal bending compliance greater than said first strut longitudinal bending compliance and length greater than said first strut length.

* * * * *